(12) United States Patent
Higashi et al.

(10) Patent No.: US 9,758,455 B2
(45) Date of Patent: Sep. 12, 2017

(54) METHOD FOR PRODUCING FLUORINATED ORGANIC COMPOUND AND FLUORINATING REAGENT

(71) Applicants: DAIKIN INDUSTRIES, LTD., Osaka (JP); NATIONAL UNIVERSITY CORPORATION HOKKAIDO UNIVERSITY, Hokkaido (JP)

(72) Inventors: Masahiro Higashi, Osaka (JP); Yosuke Kishikawa, Osaka (JP); Atsushi Shirai, Osaka (JP); Takashi Namikawa, Osaka (JP); Sumi Ishihara, Osaka (JP); Shoji Hara, Hokkaido (JP)

(73) Assignees: DAIKIN INDUSTRIES, LTD., Osaka (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 14/675,900

(22) Filed: Apr. 1, 2015

(65) Prior Publication Data
US 2015/0315136 A1 Nov. 5, 2015

(30) Foreign Application Priority Data

| Apr. 2, 2014 | (JP) | ................................ 2014-076210 |
| Aug. 22, 2014 | (JP) | ................................ 2014-169917 |

(51) Int. Cl.
| *C07C 319/20* | (2006.01) |
| *C07C 19/16* | (2006.01) |
| *C07C 23/02* | (2006.01) |
| *C07C 41/22* | (2006.01) |
| *C07C 67/307* | (2006.01) |
| *B01J 31/00* | (2006.01) |
| *C07B 39/00* | (2006.01) |
| *C07C 17/02* | (2006.01) |
| *C07C 67/287* | (2006.01) |
| *C08K 5/3432* | (2006.01) |

(52) U.S. Cl.
CPC ............... *C07C 19/16* (2013.01); *B01J 31/00* (2013.01); *C07B 39/00* (2013.01); *C07C 17/02* (2013.01); *C07C 23/02* (2013.01); *C07C 41/22* (2013.01); *C07C 67/287* (2013.01); *C07C 67/307* (2013.01); *C07C 319/20* (2013.01); *C08K 5/3432* (2013.01); *C07C 2101/14* (2013.01); *C07C 2101/20* (2013.01)

(58) Field of Classification Search
CPC ....... C07C 319/20; C07C 19/16; C07C 41/22; C07C 23/02; C07C 67/307; C07C 2101/14; C07C 2101/20; C07C 17/02; C07C 67/287; C07C 19/08; C07C 22/00; C07C 22/08; C07C 321/28; C07C 43/12; C07C 43/174; C07C 43/192; C07C 43/225; C07C 69/63; C07C 69/65; B01J 31/00; C07B 39/00; C08K 5/3432
See application file for complete search history.

(56) References Cited

U.S. PATENT DOCUMENTS

| 6,784,327 | B2 | 8/2004 | Yoneda et al. |
| 7,311,890 | B2 | 12/2007 | Yoneda et al. |
| 2003/0176747 | A1* | 9/2003 | Yoneda .................. C07B 39/00 570/175 |

FOREIGN PATENT DOCUMENTS

| JP | 2002-363110 | 12/2002 |
| JP | 2002-363111 | 12/2002 |

OTHER PUBLICATIONS

Hara et al., "IF$_5$-pyridine-HF: air- and moisture-stable fluorination reagent", Tetrahedron, vol. 68, Oct. 2, 2012, pp. 10145-10150.
Ayuba et al., "Fluorination of Sulfides Using IF$_5$-Et$_3$N-3HF", Bull. Chem. Soc. Jpn., vol. 75, 2002, pp. 1597-1603.
"Fluorination for modern indust", Speciality Chemicals Magazine, vol. 24, No. 2, 2004, pp. 28-31.
Yoneda et al., "Novel Fluorination Reagent: IF$_5$/ET$_3$N-3HF", Chemistry Letters, No. 3, 2001, pp. 222-223.
Chambers et al., "New fluorocarbon iodides", Chemical Communications, No. 23, 2001, pp. 2428-2429.
Rozen et al., "A new Method for Introducing Iodo and Bromo Fluorides into Organic Molecules using Elemental Fluorine", Journal of Organic Chemistry, vol. 50, No. 18, 1985, pp. 3342-3348.
Rozen et al., "A Novel Method for Preparation of Vicinal Fluoro-Iodo Compounds Using Elemental Fluorine", Tetrahedron Letters, vol. 21, No. 47, 1980, pp. 4543-4546.

* cited by examiner

*Primary Examiner* — Yevegeny Valenrod
*Assistant Examiner* — Blaine G Doletski
(74) *Attorney, Agent, or Firm* — Wenderoth, Lind & Ponack, L.L.P.

(57) ABSTRACT

Object: An object of the present invention is to provide a method for producing, with a high yield, a fluorinated organic compound, the fluorinated organic compound having not been produced with a sufficient yield by a conventional method for producing a fluorinated organic compound using a fluorinating agent containing IF$_5$-pyridine-HF alone. Another object of the present invention is to provide a fluorinating reagent.
Means for achieving the object: A method for producing a fluorinated organic compound comprising step A of fluorinating an organic compound by bringing the organic compound into contact with (1) IF$_5$-pyridine-HF and (2) at least one additive selected from the group consisting of amine hydrogen fluorides, $X^aF$ (wherein $X^a$ represents hydrogen, potassium, sodium, or lithium), oxidizers, and reducing agents.

4 Claims, No Drawings

METHOD FOR PRODUCING FLUORINATED ORGANIC COMPOUND AND FLUORINATING REAGENT

TECHNICAL FIELD

The present invention relates to a process for producing a fluorinated organic compound, and a fluorinating reagent.

BACKGROUND ART

Fluorine compounds are extremely important as chemical products such as functional materials, compounds for medicines and agrochemicals, and electronic materials, the intermediates of the chemical products, or the like.

Fluoride, hydrogen fluoride, sulfur tetrafluoride, etc., have been used as fluorinating agents to obtain a target fluorine compound by fluorinating a various organic compound as a starting material. These fluorinating agents, however, are difficult to handle due to their toxicity, corrosiveness, explosion risk at the time of reaction, etc., and thus require special devices or techniques.

A reaction for introducing a fluorine atom into an organic compound by utilizing nucleophilic substitution with a fluoride ion has recently been developed, in addition to various fluorinating agents used for the reaction.

For example, iodine pentafluoride ($IF_5$) is known as a powerful fluorinating agent with high oxidizability; however, it is a dangerous liquid fluorinating agent because it reacts with moisture in air and decomposes while generating HF. Non-patent Literature 1 recently reported that $IF_5$ having such features becomes a stable white solid ($IF_5$-pyridine-HF) in air when mixed with pyridine HF, and is effective for fluorination of various sulfur compounds.

CITATION LIST

Non-Patent Literature

NPL 1: S. Hara, M. Monoi, R. Umemura, C. Fuse, Tetrahedron, 2012, 68, 10145-10150

SUMMARY OF INVENTION

Technical Problem

Although $IF_5$-pyridine-HF is an excellent fluorinating agent, some fluorinated organic compounds cannot be produced with a sufficient yield by the method for producing a fluorinated organic compound using a fluorinating agent containing $IF_5$-pyridine-HF alone. Accordingly, an improved method for producing a fluorinated organic compound and an improved fluorinating agent are desired.

Therefore, an object of the present invention is to provide a method for producing, with a high yield, a fluorinated organic compound, the fluorinated organic compound having not been produced with a sufficient yield by a conventional method for producing a fluorinated organic compound using a fluorinating agent containing $IF_5$-pyridine-HF alone. Another object of the present invention is to provide a fluorinating reagent.

Solution to Problem

As a result of extensive research, the inventors found that the above object can be achieved by a method for producing a fluorinated organic compound comprising step A of fluorinating an organic compound by bringing the organic compound into contact with (1) $IF_5$-pyridine-HF and (2) at least one additive selected from the group consisting of amine/hydrogen fluoride salt, $X^aF$ (wherein $X^a$ represents hydrogen, lithium, sodium, or potassium), oxidizers, and reducing agents. The inventors conducted further research to accomplish the present invention.

The present invention includes the following embodiments.

Item 1. A method for producing a fluorinated organic compound comprising step A of fluorinating an organic compound by bringing the organic compound into contact with (1) $IF_5$-pyridine-HF and (2) at least one additive selected from the group consisting of amine/hydrogen fluoride salt, $X^aF$ (wherein $X^a$ represents hydrogen, potassium, sodium, or lithium), oxidizers, and reducing agents.

Item 2. The method according to Item 1, wherein the additive is $Et_3N$-nHF (wherein n is a real number of 1 to 9).

Item 3. A fluorinating reagent comprising (1) $IF_5$-pyridine-HF and (2) at least one additive selected from the group consisting of amine/hydrogen fluoride salt, $X^aF$ (wherein $X^a$ represents hydrogen, potassium, sodium, or lithium), oxidizers, and reducing agents.

Item 4. The fluorinating reagent according to Item 3, wherein the additive is $Et_3N$-nHF (wherein n is a real number of 1 to 9).

The method for producing a fluorinated organic compound and the fluorinating reagent of the present invention are detailed below.

Method for Producing a Fluorinated Organic Compound

The method for producing a fluorinated organic compound of the present invention comprises step A of fluorinating an organic compound by bringing the organic compound into contact with (1) $IF_5$-pyridine-HF and (2) at least one additive selected from the group consisting of amine/hydrogen fluoride salt, $X^aF$ (wherein $X^a$ represents hydrogen, potassium, sodium, or lithium), oxidizers, and reducing agents.

In the present invention, examples of the organic compound include (1) compounds having an OH group;
(2) ketones (including diketone, β-ketocarboxylic acid, β-ketoester), aldehydes, Schiff base, hydrazone and like imines, or esters;
(3) sulfides;
(4) epoxies;
(5) aromatic compounds (e.g., phenylhydrazine derivatives, phenol derivatives, 2-naphthol derivatives, or aniline derivatives);
(6) thiocarbonyl compounds; and
(7) unsaturated carbon compounds (e.g., olefin compounds).

The fluorination of organic compounds in the present invention includes replacement of a hydrogen atom with a fluorine atom, and replacement of the following atom or group with a fluorine atom as shown in each set of parenthesis: hydrogen atom (CH→CF), carbonyl group (CO→$CF_2$), hydrazino group (C—NHNH$_2$→C—F; C=N—NH$_2$→$CF_2$), hydroxyl group (C—OH→C—F), and epoxy group (C—O—→C—F).

Fluorination conducted in the production method of the present invention is exemplified. Fluorinated organic compounds obtained by the production method below of the present invention are also exemplified.

(1) Fluorination of Compounds Having an OH Group

In the fluorination, the following reactions, for example, are conducted.

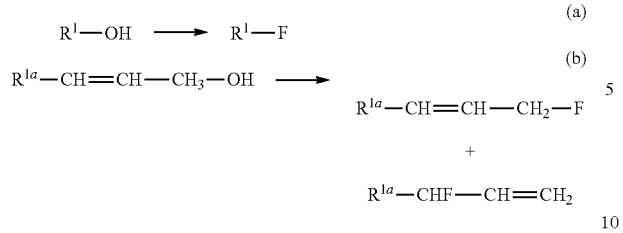

(In the above formulae, $R^1$ represents an alkyl group that may have at least one substituent, an aralkyl group that may have at least one substituent, an alkenyl group that may have at least one substituent, an acyl group, a cycloalkyl group that may have at least one substituent, or a heterocycloalkyl group that may have at least one substituent. $R^{1a}$ represents an alkyl group that may have at least one substituent, an aryl group that may have at least one substituent, an aralkyl group that may have at least one substituent, an alkenyl group that may have at least one substituent, an acyl group, a cycloalkyl group that may have at least one substituent, or a heterocycloalkyl group that may have at least one substituent).

In the present specification, "may have a substituent" includes both cases where a substituent is contained (i.e., substituted) and not contained (unsubstituted). For example, an alkyl group that may have at least one substituent includes alkyl groups (i.e., unsubstituted alkyl groups) and alkyl groups having a substituent (i.e., substituted alkyl groups).

Specific examples of compounds having an OH group include alcohols including aliphatic alcohols, such as methanol, ethanol, n-propanol, isopropanol, n-butanol, isobutanol, tert-butanol, pentanol, hexanol, octanol, decanol, palmityl alcohol, stearyl alcohol, and oleyl alcohol; alicyclic alcohols, such as benzyl alcohol, a mono-, di- or trisaccharide having at least one non-protected hydroxyl group, cyclohexyl alcohol, and ascorbic acid; steroid alcohols, such as cholesterol, cholic acid, and cortisone; and carboxylic acids including aliphatic monocarboxylic acids, such as acetic acid, trifluoroacetic acid, propionic acid, acrylic acid, methacrylic acid, crotonic acid, butyric acid, valeric acid, isovaleric acid, pivalic acid, lauric acid, myristic acid, palmitic acid, stearic acid, oleic acid, linoleic acid, linolenic acid, and cinnamic acid; polycarboxylic acids, such as oxalic acid, succinic acid, malonic acid, glutaric acid, adipic acid, maleic acid, fumaric acid, and citric acid; aromatic carboxylic acids, such as benzoic acid, salicylic acid, (o-, m-, p-)phthalic acid, nalidixic acid, and nicotinic acid; vitamins having carboxylic acid groups, such as pantothenic acid and biotin; 20 kinds of natural amino acids, such as glycine, alanine, phenylalanine, cysteine, aspartic acid, glutamic acid, threonine, histidine, lysine, methionine, and proline; and hydroxycarboxylic acids, such as lactic acid, citric acid, malic acid, and tartaric acid.

(2) Fluorination of Ketones (Including Diketone, β-Ketocarboxylic Acid, β-Ketoester), Aldehydes, Imines Such as Schiff Base and Hydrazone, and Esters In the fluorination, the following reactions, for example, are conducted.

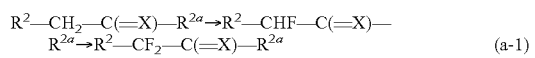

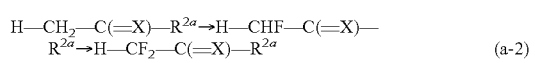

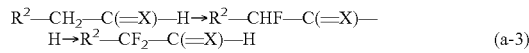

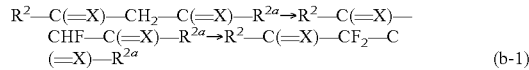

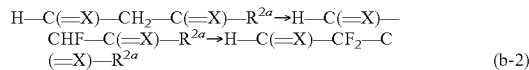

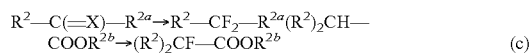

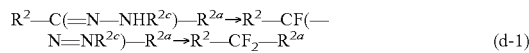

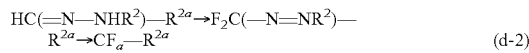

(In the above formulae, X represents O or NR' (R' represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, an amino group, a monoalkylamino group that may have at least one substituent, a dialkylamino group that may have at least one substituent, an acyl group, or an acylamino group. $R^2$, $R^{2a}$, and $R^{2c}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, a monoalkylamino group that may have at least one substituent, a dialkylamino group that may have at least one substituent, an acyl group, or an acylamino group. $R^2$ and $R^{2a}$ may bond to each other to form a ring structure).

$R^{2b}$ represents an alkyl group that may have at least one substituent, an aralkyl group that may have at least one substituent, or an aryl group that may have at least one substituent).

Examples of substances having a ring structure include 4 to 7-membered rings of an aliphatic group that may have at least one substituent.

Examples of ketones include acetone, methyl ethyl ketone, acetylacetone, acetoacetic acid, acetoacetate, cyclohexanone, acetophenone, benzophenone, propiophenone, 4-piperidone, 1-oxo-1,2-dihydronaphthalene, benzylideneacetophenone(chalcone), deoxybenzoin, and ketals thereof, etc.

Examples of aldehydes include acetoaldehyde, propionaldehyde, butylaldehyde, isobutylaldehyde, valeraldehyde, isovaleraldehyde, acrylaldehyde, benzaldehyde, cinnamaldehyde, anisaldehyde, nicotinealdehyde, and acetals thereof, etc.

Examples of imines of Schiff base, hydrazone, and the like include condensates of ketone or aldehyde with an appropriate primary amine.

Examples of esters include methyl isobutyrate, ethyl isobutylate, etc.

(3) Fluorination of Sulfides (Including Dithioacetal and Dithioketal)

In the fluorination, one or two hydrogen atoms of methylene that is located adjacent to a sulfur atom are substituted with fluorine atoms, or a sulfur atom is substituted with fluorine.

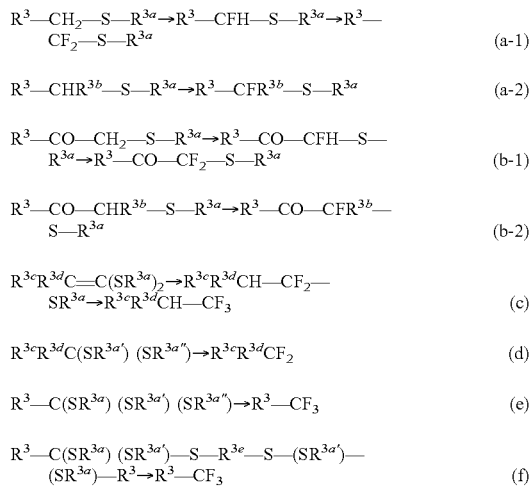

(In the above formulae, $R^{3a}$, $R^{3a'}$, and $R^{3a''}$ may be the same or different, and each represents an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, or a heterocyclic group that may have at least one substituent. Alternately, $R^{3a}$ and $R^{3a'}$ bond to each other may represent 4 to 7-membered rings of an aliphatic group that may have at least one substituent. $R^3$ and $R^{3b}$ may be the same or different, and each represents an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, an amino group, a monoalkylamino group that may have at least one substituent, a dialkylamino group that may have at least one substituent, an acyl group, an acylamino group, a cyano group, an alkylsulfinyl group that may have at least one substituent, an aralkylsulfinyl group that may have at least one substituent, an arylsulfinyl group that may have at least one substituent, a cycloalkylsulfinyl group that may have at least one substituent, a heterocycloalkylsulfinyl group that may have at least one substituent, a sulfinyl group bonded by a heterocyclic group that may have at least one substituent, an alkylsulfonyl group that may have at least one substituent, an aralkylsulfonyl group that may have at least one substituent, an arylsulfonyl group that may have at least one substituent, a cycloalkylsulfonyl group that may have at least one substituent, a heterocycloalkylsulfonyl group that may have at least one substituent, or a sulfonyl group bonded by a heterocyclic group that may have at least one substituent. Alternately, $R^3$ and $R^{3b}$ may form 4 to 8-membered rings with carbon atoms with or without having a heteroatom in the ring. (The ring may be substituted with at least one substituent selected from the group consisting of a halogen atom, an oxo group, an alkyl group that may have at least one substituent, an aralkyl group that may have at least one substituent, an aryl group that may have at least one substituent, an alkenyl group that may have at least one substituent, a cyano group, and an amino group.) $R^{3c}$ and $R^{3d}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, a monoalkylamino group that may have at least one substituent, a dialkylamino group that may have at least one substituent, an acyl group, or an acylamino group. Alternately, $R^{3c}$ and $R^{3d}$ may bind to an adjacent carbon atom to form a saturated or unsaturated 4 to 7-membered rings of an aliphatic group that may have at least one substituent. (The ring may be substituted with at least one member selected from the group consisting of a halogen atom, an oxo group, an alkyl group that may have at least one substituent, an aralkyl group that may have at least one substituent, an aryl group that may have at least one substituent, an alkenyl group that may have at least one substituent, a cyano group, and an amino group.))

Examples of sulfide compounds include methyl ethyl sulfide, methyl benzyl sulfide, 2-phenylthioacetate, 2-phenylthioacetophenone, 2-(methylthio)acetophenone, bis(methylthio)methylbenzene, 2-octyl-1,3-dithiane, 2-phenyl-2-trifluoromethyl-1,3-dithiolane, tris(ethylthio)hexane, 4-tris(methylthio)toluene, etc.

(4) Fluorination of Olefin Compounds or Epoxy Compounds

In the fluorination, the following fluorine addition reaction, for example, is conducted.

(In the above formula, $R^4$, $R^{4a}$, $R^{4b}$, and $R^{4c}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, or a heterocyclic group that may have at least one substituent).

Examples of olefines include tetrafluoroethylene, methyl acrylate, methyl methacrylate, etc.

Examples of epoxy compounds include oxirane, 1,2-epoxyethylbenzene, 1-chloro-2,3-epoxypropane, α,α'-epoxybibenzyl, etc.

(5) Fluorination of Aromatic Compounds

In the fluorination, a fluorine substituent is introduced in an aromatic ring by, for example, the following reaction. Fluorination of an aromatic ring in a phenol derivative or aniline derivative can be carried out by fluorinating it, then reducing it by zinc powder or like reducing agents, to obtain the targeted fluorine compound.

(5-1) Fluorination of Phenylhydrazine Derivatives

A phenylhydrazine residue that may have at least one substituent can be substituted with a fluorine atom.

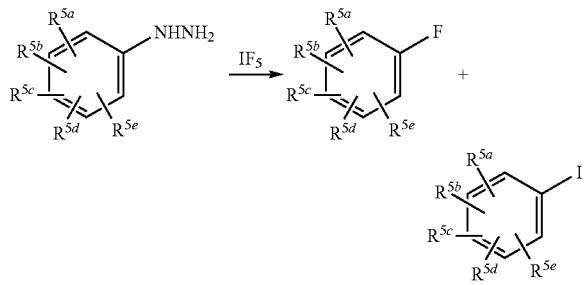

(In the above formula, $R^{5a}$, $R^{5b}$, $R^{5c}$, $R^{5d}$, and $R^{5e}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

(5-2) Fluorination of Phenol Derivatives

A phenol derivative forms the difluorinated quinonoid structure as shown below by reacting with $IF_5$. Thereafter, by reducing the resultant compound, a phenol derivative having fluorine introduced in the ortho- or para-position is produced.

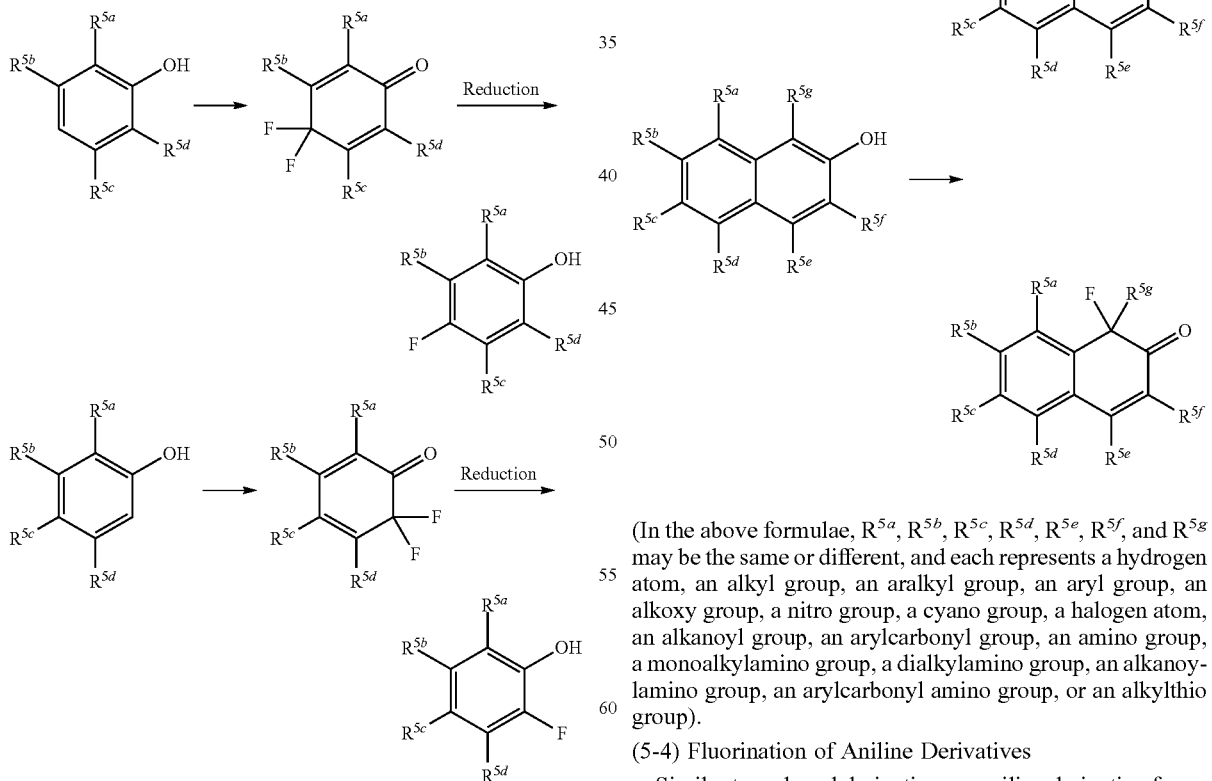

(In the above formulae, $R^{5a}$, $R^{5b}$, $R^{5c}$, and $R^{5d}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

In a starting material in which all atoms or groups in the ortho- and para-positions are substituted, fluorine atoms are introduced into the ortho- or para-position, forming compounds having a fluorine quinonoid structure.

In the above example, phenol that may have at least one substituent is used as a phenol derivative; however, it is also possible to introduce fluorine atoms into benzene-based aromatic compounds or condensed polycyclic hydrocarbons that may be substituted and have electron-releasing groups such as a hydroxyl group or an alkoxy group.

(5-3) Fluorination of 2-Naphthol Derivatives

A carbon atom in the 1-position of naphthol can be subjected to mono- or difluorination.

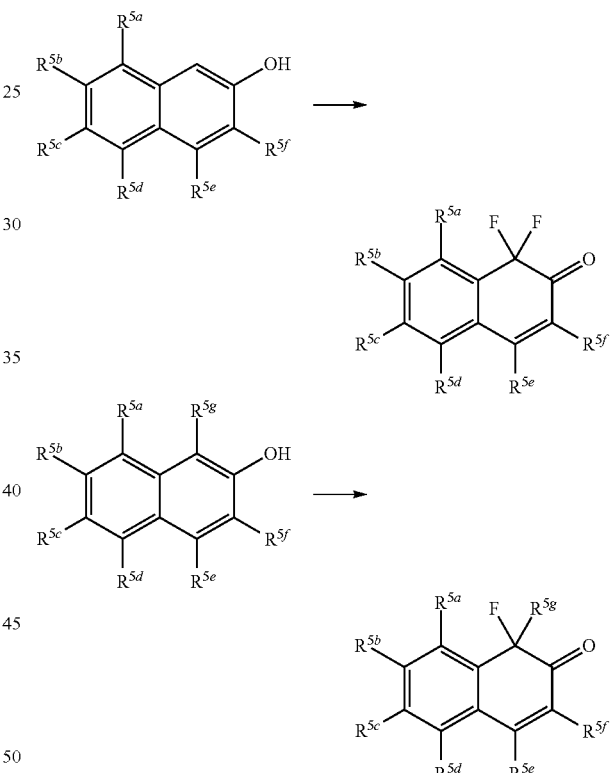

(In the above formulae, $R^{5a}$, $R^{5b}$, $R^{5c}$, $R^{5d}$, $R^{5e}$, $R^{5f}$, and $R^{5g}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

(5-4) Fluorination of Aniline Derivatives

Similar to a phenol derivative, an aniline derivative forms the difluorinated quinonoid structure as shown below by reacting with $IF_5$. Then, by reducing the resultant compound, an aniline derivative having fluorine introduced in the ortho- or para-position is produced.

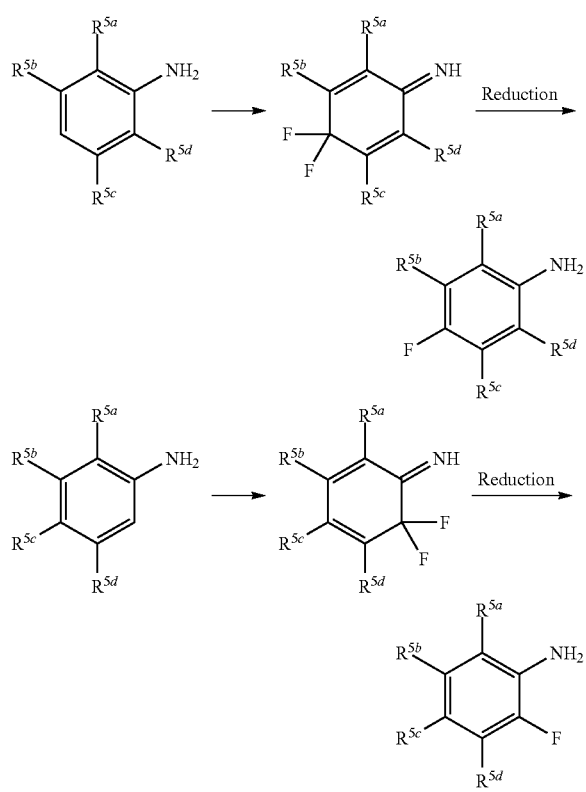

(In the above formulae, $R^{5a}$, $R^{5b}$, $R^{5c}$, and $R^{5d}$ may be the same or different, and each represents a hydrogen atom, an alkyl group, an aralkyl group, an aryl group, an alkoxy group, a nitro group, a cyano group, a halogen atom, an alkanoyl group, an arylcarbonyl group, an amino group, a monoalkylamino group, a dialkylamino group, an alkanoylamino group, an arylcarbonyl amino group, or an alkylthio group).

Using aniline that may have at least one substituent or naphthylamine that may have at least one substituent as an aniline derivative also allows a fluorine atom to be introduced into an aromatic ring.

(6) Fluorination of Thiocarbonyl Compounds (Including Thioketone, Thioester, Thiocarbonic Ester, Thioamide, Dithiocarboxylate, and Dithiocarbamate)

The following reactions are conducted.

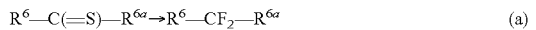  (a)

  (b)

(In the above formulae, $R^6$ and $R^{6a}$ may be the same or different, and each represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, a monoalkylamino group that may have at least one substituent, a dialkylamino group that may have at least one substituent, an acyl group, or an acylamino group. $R^6$ and $R^{6a}$ may bond to each other to form a ring structure. $R^{6b}$ represents an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, or a heterocyclic group that may have at least one substituent).

Examples of thiocarbonyl compounds include O-(4-isopropylphenyl)S-methyl dithiocarbonate, O-(4-bromophenyl)S-methyl dithiocarbonate, ethyl 4-(((methylthio)carbonothioyl)oxy)benzoate, O-decyl S-methyl dithiocarbonate, O-(3-phenylpropyl)S-methyl dithiocarbonate, O-methyl cyclohexanecarbothioate, O-propyl1-piperidinecarbothioate, methyl dithiobenzoate, thiobenzophenone, O-phenyl thiobenzoate, N,N-dimethylphenylthioamide, ethyl 3-quinolinedithiocarboxylate, trifluoromethane carbothioyl naphthalene, N-methyl-N-phenyl trifluoromethanethioamide, N-benzyl-N-phenylheptafluoropropane thioamide, O-(4'-pentyl-[1,1'-bi(cyclohexane)]-4-yl)S-methyl dithiocarbonate,

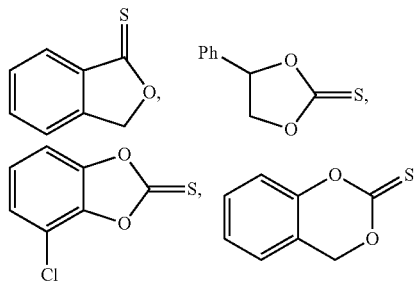

etc.

(7) Polyfluorination of Ethyl Portion of —COOR Group-Containing Ethylsulfides

In the fluorination, an ethyl portion located adjacent to an S atom is polyfluorinated.

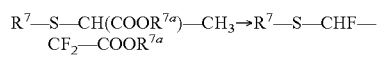

(In the above formula, $R^7$ represents an aryl group that may have at least one substituent or an aromatic heterocyclic group that may have at least one substituent. $R^{7a}$ represents a hydrogen atom, an alkyl group that may have at least one substituent, an aralkyl group that may have at least one substituent, an aryl group that may have at least one substituent, an alkenyl group that may have at least one substituent, a cycloalkyl group that may have at least one substituent, a heterocycloalkyl group that may have at least one substituent, a heterocyclic group that may have at least one substituent, an alkoxy group that may have at least one substituent, an aryloxy group that may have at least one substituent, an amino group, a monoalkylamino group that may have at least one substituent, a dialkylamino group that may have at least one substituent, an acyl group, an acylamino group, a cyano group, an alkylsulfinyl group that may have at least one substituent, an aralkylsulfinyl group that may have at least one substituent, an arylsulfinyl group that may have at least one substituent, a cycloalkylsulfinyl group that may have at least one substituent, a heterocycloalkylsulfinyl group that may have at least one substituent, a sulfinyl group bonded by a heterocyclic group that may have at least one substituent, an alkylsulfonyl group that may have at least one substituent, an aralkylsulfonyl group that may have at least one substituent, an arylsulfonyl group that may have at least one substituent, a cycloalkylsulfonyl group that may have at least one substituent, a heterocycloalkylsulfonyl group that may have at least one substituent, or a sulfonyl group bonded to a heterocyclic group that may have at least one substituent).

Examples of —COOR group-containing ethylsulfides include 2-((4-chlorophenyl)thio)ethyl propanate.

(8) Fluorination of Unsaturated Carbon Compound.

In the fluorination, fluorine or iodine is added to a carbon-carbon double bond or carbon-carbon triple bond.

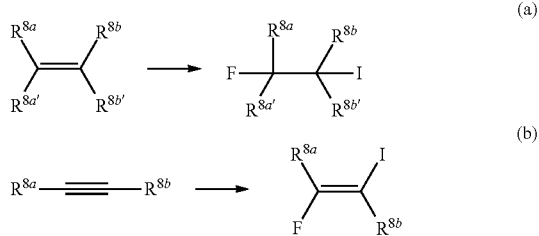

(In the above formulae, $R^{8a}$, $R^{8a'}$, $R^{8b}$, and $R^{8b'}$ may be the same or different, and each represents a hydrogen atom, an alkyl group that may have at least one substituent, an aryl group that may have at least one substituent, an aralkyl group that may have at least one substituent, an alkenyl group that may have at least one substituent, an acyl group, a cycloalkyl group that may have at least one substituent, a heterocycloalkyl group that may have at least one substituent, an ester group, or a halogen atom. At least two of the $R^{8a}$, $R^{8a'}$, $R^{8b}$, and $R^{8b'}$ may be bonded from one another to form a cyclic structure.)

Examples of the cyclic structure include 4 to 12-membered rings of an aliphatic group that may have at least one substituent.

Examples of the unsaturated carbon compound include $C_{2-20}$ unsaturated carbon compounds such as decene, cyclodecene, dodecyne, phenylacetylene, 4-octyne, 10-undecen-1-yl acetate, 10-undecynoic acid isopropyl ester, and 3-cyclohexylpropine.

Examples of alkyl groups include methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and like straight or branched $C_1$-$C_{18}$ alkyl groups. Preferable examples include methyl, ethyl, n-propyl, isopropyl, n-butyl, isobutyl, sec-butyl, tert-butyl, pentyl, hexyl and like straight or branched $C_1$-$C_6$ alkyl groups.

Examples of alkoxy groups include methoxy, ethoxy, n-propoxy, isopropoxy, n-butoxy, isobutoxy, sec-butoxy, tert-butoxy, pentyloxy, hexyloxy and like straight or branched $C_1$-$C_6$ alkoxy groups.

Examples of alkenyl groups include a vinyl group, an allyl group, a 3-butenyl group and like $C_{2-6}$ alkenyl groups, etc.

Examples of halogens include a fluorine atom, a chlorine atom, a bromine atom, an iodine atom, etc.

Examples of aryl groups include a phenyl group, a naphthyl group, etc.

Examples of aryloxy groups include a phenoxy group, a naphthyloxy group, etc.

Examples of aralkyl groups include 2-phenylethyl, benzyl, 1-phenylethy, 3-phenylpropyl, 4-phenylbutyl and like $C_{7-10}$ aralkyl groups, etc.

Examples of cycloalkyl groups include cyclopropyl, cyclobutyl, cyclopentyl, cyclohexyl, cycloheptyl, cyclooctyl and like $C_3$-$C_8$ cycloalkyl groups, etc. Preferable are $C_3$-$C_7$ cycloalkyl groups.

Examples of heterocycloalkyl groups include substances in which one or more ring-constituting carbon atoms of cycloalkyl groups are replaced by atoms of nitrogen, oxygen, sulfur, etc.

Examples of monoalkylamino groups include amino groups monosubstituted with the above-described $C_1$-$C_6$ alkyl groups.

Examples of dialkylamino groups include dimethylamino, diethylamino, di-n-propylamino, diisopropylamino, dibutylamino, dipentylamino, dihexylamino and like amino groups di-substituted with the above-described $C_1$-$C_6$ alkyl groups.

Examples of acylamino groups include formylamino, benzoylamino, acetylamino, propionylamino, n-butyrylamino and like $C_1$-$C_8$ acylamino groups (e.g., formylamino, alkanoylamino, and arylcarbonylamino).

Examples of alkylthio groups include —S—($C_1$-$C_6$ alkyl groups), etc. ($C_1$-$C_6$ alkyl groups are the same as described above.)

Examples of heterocyclic groups include piperidyl, furyl, thienyl, imidazolyl, oxazolyl, triazolyl, pyrrolyl, pyrrolidinyl, triazolyl, benzothiazolyl, benzoimidazolyl, oxadiazolyl, thiadiazolyl, indolyl, pyrazolyl, pyridazinyl, cinnolinyl, quinolyl, isoquinolyl, quinoxalinyl, pyradinyl, pyridyl, benzofuryl, benzothienyl, tetrazolyl and like 5 to 10-membered monocyclic or bicyclic heterocyclic groups having at least one hetero atom selected from nitrogen, oxygen, and sulfur as a ring constituting atom.

Of the heterocyclic groups, examples of aromatic heterocyclic groups include furyl, thienyl, imidazolyl, oxazolyl, thiazolyl, pyrrolyl, triazolyl, benzothiazolyl, benzoimidazolyl, oxadiazolyl, thiadiazolyl, indolyl, pyrazolyl, pyridazinyl, cinnolinyl, quinolinyl, isoquinolinyl, quinoxalinyl, pyradinyl, pyridyl, benzofuryl, benzothienyl, tetrazolyl and like 5 to 10-membered monocyclic or bicyclic heteroaryl groups having at least one hetero atom selected from nitrogen, oxygen, and sulfur as a ring constituting atom.

Examples of acyl groups include formyl group; acetyl, propionyl, n-butyryl, isobutyryl, valeryl, isovaleryl, pivaloyl and like straight or branched $C_{2-6}$ alkanoyl groups; and benzoyl and like $C_7$-$C_{15}$ arylcarbonyl groups.

Specific examples of an alkyl group, an aralkyl group, an aryl group, a cycloalkyl group, a heterocycloalkyl group, and a heterocyclic group in an alkylsulfinyl group, an aralkylsulfinyl group, an arylsulfinyl group, a cycloalkylsulfinyl group, a heterocycloalkylsulfinyl group, and a sulfinyl group having a heterocyclic group bonded thereto are as described above.

Specific examples of an alkyl group, an aralkyl group, an aryl group, a cycloalkyl group, a heterocycloalkyl group, and a heterocyclic group in an alkylsulfonyl group, an aralkylsulfonyl group, an arylsulfonyl group, a cycloalkylsulfonyl group, a heterocycloalkylsulfonyl group, and a sulfonyl group having a heterocyclic group bonded thereto are as described above.

Examples of esters include an acyl-O-group and an alkoxy-CO-group. Herein, the above-mentioned "acyl groups" and "alkoxy groups" can be used as "acyl" and "alkoxy."

The number of substituents in an alkyl group having at least one substituent, an alkoxy group having at least one substituent, or an alkenyl group having at least one substituent is 1 to 5, and preferably 1 to 3. Examples of the substituent include halogen, $C_1$-$C_6$ alkoxy, $C_1$-$C_6$ alkylthio, cyano, nitro, an amino group, a hydroxyl group, a $C_1$-$C_6$ alkyl-carbonyloxy group (e.g., acetoxy), a $C_1$-$C_6$ alkoxycarbonyl group (e.g., isopropyloxycarbonyl), a $C_3$-$C_6$ cycloalkyl group (e.g., cyclohexyl), and the like. Examples of an alkyl group having a halogen include an alkyl group in which a part or all of the hydrogen atoms are substituted with fluorine.

The number of substituents in an aralkyl group having at least one substituent, an aryl group having at least one substituent, an aryloxy group having at least one substituent, a cycloalkyl group having at least one substituent, a heterocycloalkyl group having at least one substituent, a heterocyclic group having at least one substituent, a monoalkylamino group having at least one substituent, a dialkylamino group having at least one substituent, an acylamino group, an alkylsulfinyl group having at least one substituent, an aralkylsulfinyl group having at least one substituent, an arylsulfinyl group having at least one substituent, a cycloalkylsulfinyl group having at least one substituent, a heterocycloalkylsulfinyl group having at least one substituent, a sulfinyl group to which a heterocyclic group having at least one substituent is bonded, an alkylsulfonyl group having at least one substituent, an aralkylsulfonyl group having at least one substituent, an arylsulfonyl group having at least one substituent, a cycloalkylsulfonyl group having at least one substituent, a heterocycloalkylsulfonyl group having at least one substituent, or a sulfonyl group to which a heterocyclic group having at least one substituent is bonded is 1 to 5, and preferably 1 to 3. Examples of the substituent include $C_1$-$C_6$ alkyl groups, a halogen atom, $C_1$-$C_6$ alkoxy groups, $C_1$-$C_6$ alkylthio, cyano, nitro, an amino group, a hydroxyl group, and the like.

The number of substituents in 4 to 7-membered rings of an aliphatic group having at least one substituent is 1 to 5, and preferably 1 to 3. Examples of substituents include $C_1$-$C_6$ alkyl groups, a halogen atom, $C_1$-$C_6$ alkoxy groups, $C_1$-$C_6$ alkylthio, cyano, nitro, an amino group, a hydroxyl group, carboxy ester, and the like. In addition,

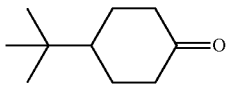

is also included in a 4 to 7-membered ring of an aliphatic group having at least one substituent.

Examples of acyl groups include chloroacetyl group, bromoacetyl group, dichloroacetyl group, trifluoroacetyl group and like substituted acetyl groups; methoxyacetyl group, ethoxyacetyl group and like alkoxy-substituted acetyl groups; methylthioacetyl group and like alkylthio-substituted acetyl groups; phenoxyacetyl group, phenylthioacetyl group, 2-chlorobenzoyl group, 3-chlorobenzoyl group, 4-chlorobenzoyl group, 4-methylbenzoyl group, 4-t-butylbenzoyl group, 4-methoxybenzoyl group, 4-cyanobenzoyl group, 4-nitrobenzoyl group and like substituted benzoyl groups, etc.

$IF_5$-pyridine-HF used in the production method of the present invention is a known substance disclosed in Non-patent Literature 1.

$IF_5$-pyridine-HF is a complex constituted by (1) $IF_5$, (2) 1 mol of pyridine per mol of $IF_5$, and (3) 1 mol of HF per mol of $IF_5$.

$IF_5$-pyridine-HF can be produced according to the method disclosed in Non-patent Literature 1.

Specifically, $IF_5$-pyridine-HF can be obtained by mixing $IF_5$ with pyridine-HF (pyridine 50 mol %, HF 50 mol %). Pyridine HF (pyridine 50 mol %, HF 50 mol %) can be obtained by adding pyridine to an equivalent mol of anhydrous HF.

As long as the effect of the present invention is not significantly impaired, the reaction system used in the production method of the present invention may contain $IF_5$, pyridine, HF, or a combination thereof, which do not constitute the $IF_5$-pyridine-HF.

In the production method of the present invention, at least one additive selected from the group consisting of amine/hydrogen fluoride salt, $X^aF$ (wherein $X^a$ represents hydrogen, potassium, sodium, or lithium), oxidizers, and reducing agents is used together with $IF_5$-pyridine-HF.

The additive presumably functions as a reaction accelerator in the production method of the present invention; however, the present invention is not limited thereto.

Of the additives, the mechanism in which a reducing agent functions as a reaction accelerator is presumably based on the addition of IF generated from $IF_5$ in the $IF_5$-pyridine-HF in the reaction system to an organic compound, which is a substrate; however, the present invention is not limited thereto.

The additive is preferably an amine/hydrogen fluoride salt or a reducing agent. In a preferable embodiment of the production method of the present invention, the additive is a reducing agent.

Examples of amine/hydrogen fluoride salt include primary amine/hydrogen fluoride salt, secondary amine/hydrogen fluoride salt, and tertiary amine/hydrogen fluoride salt.

Preferable examples of amine/hydrogen fluoride salt include aliphatic primary amine/hydrogen fluoride salt, aliphatic secondary amine/hydrogen fluoride salt, and aliphatic tertiary amine/hydrogen fluoride.

Specific examples of aliphatic primary amines in the aliphatic amine/hydrogen fluoride salt include methylamine, ethylamine, propylamine, butylamine, pentylamine, hexylamine, etc.

Specific examples of aliphatic secondary amines in the aliphatic amine/hydrogen fluoride salt include dimethylamine, diethylamine, dipropylamine, dibutylamine, dipentylamine, dihexylamine, etc.

Specific examples of aliphatic tertiary amines in aliphatic tertiary amine/hydrogen fluoride salt include trimethylamine, triethylamine, diisopropylethylamine, tributylamine, N,N,N',N'-tetramethylethylenediamine, etc.

Preferable examples of aliphatic groups of the aliphatic primary amine/hydrogen fluoride salt, aliphatic secondary amine/hydrogen fluoride salt, and aliphatic tertiary amine/hydrogen fluoride salt include methyl, ethyl, and butyl. More preferable examples include ethyl and butyl.

Amine/hydrogen fluoride salt are preferably tertiary amine/hydrogen fluoride salt, and more preferably aliphatic tertiary amine/hydrogen fluoride salt, and particularly preferably triethylamine/hydrogen fluoride salt.

Examples of triethylamine/hydrogen fluoride salt include $Et_3$ N-nHF (n is a real number of 1 to 9).

Examples of oxidizers include iodine, bromine, chlorine, etc.

Examples of reducing agents include hydrazine, formic acid, amines (e.g., primary amines such as methylamine, ethylamine, propylamine, butylamine, pentylamine, hexylamine, cyclohexylamine, and ethylenediamine; secondary amines such as dimethylamine, diethylamine, dipropylamine, dibutylamine, dipentylamine, dihexylamine, and dicyclohexylamine; tertiary amines such as trimethylamine, triethylamine, diisopropylethylamine, tributylamine, N,N,N',N'-tetramethylethylene diamine, triphenylamine, diphenyl methylamine), potassium iodide, sodium iodide, lithium iodine, catechols that may have a substituent (e.g., catechols that may have at least one $C_1$-$C_3$ alkyl group such as catechol and methylcatechol), hydroquinones that may have a substituent (e.g., hydroquinones that may have at least one $C_1$-$C_3$ alkyl group such as hydroquinone and methyl hydroquinone), pyrogallols (e.g., pyrogallol that may have at least one $C_1$-$C_3$ alkyl group such as pyrogallol and methyl pyrogallol), palladium carbon (Pd/C), tin (Sn), triphenyl phosphine (PPh$_3$), magnesium (Mg), aluminum (Al), etc. Preferable examples thereof include potassium iodide, catechols that may have a substituent (catechols that may have at least one $C_1$ to $C_3$ alkyl group such as catechol and methylcatechol), hydroquinones that may have a substituent (e.g., hydroquinones that may have at least one $C_1$-$C_3$ alkyl group such as hydroquinone and methyl hydroquinone), Pd/C, Sn (turnings), triphenyl phosphine (PPh$_3$), magnesium (Mg), and aluminum (Al). More preferable examples thereof include potassium iodide (KI), catechols that may have a substituent (e.g., catechols that may have at least one $C_1$ to $C_3$ alkyl group such as catechol and methylcatechol) and hydroquinones that may have a substituent (e.g., hydroquinones that may have at least one $C_1$-$C_3$ alkyl group such as hydroquinone and methyl hydroquinone).

The additive used in the production method of the present invention is preferably Et$_3$N-nHF (wherein n is a real number of 1 to 9).

The amount of the IF$_5$-pyridine-HF used in Step A is preferably in the range of 1 to 10 mol, more preferably 1 to 5 mol, and even more preferably 1.5 to 3 mol per mol of the organic compound, which is a starting material compound.

The amount of the additive used in Step A is preferably in the range of 0.01 to 10 mol, more preferably in the range of 0.1 to 5 mol, and even more preferably in the range of 0.1 to 2 mol per mol of the IF$_5$-pyridine-HF.

Step A in the production method of the present invention can be preferably performed in air. The air may be an ordinal air that has not been dried. Accordingly, the production method of the present invention can be performed at low cost, and is industrially advantageous.

The reaction temperature of Step A in the production method of the present invention is generally in the range of −20 to 140° C., preferably in the range of 0 to 120° C., and more preferably in the range of 20 to 100° C.

The reaction time of Step A in the production method of the present invention is generally in the range of 0.5 to 48 hours, preferably in the range of 1 to 24 hours, and more preferably in the range of 2 to 24 hours.

The production method of the present invention is preferably performed in the presence of a reaction solvent.

Examples of the reaction solvent include methylene chloride, tetrachloroethane, chloroform, carbon tetrachloride, cyclohexane, and mixed solvents of two or more of these.

The amount of the reaction solvent used in Step A is in the range of 5 to 50 parts by weight, and more preferably in the range of 10 to 30 parts by weight per part by weight of the organic compound which is a starting compound.

The production method of the present invention can be carried out in air by adding, to a reaction solvent and IF$_5$-pyridine-HF that have been placed in a reactor, an organic compound having at least one hydrogen atom.

The fluorinated organic compound produced by the method of the present invention can be generated by a known method, such as extraction.

Fluorinating Reagent

The fluorinating reagent of the present invention contains at least one additive selected from the group consisting of (1) IF$_5$-pyridine-HF, and (2) amine/hydrogen fluoride salt, $X^a$F (wherein $X^a$ is a hydrogen atom, sodium, potassium, or lithium), oxidizers, and reducing agents.

In a preferable embodiment of the fluorinating reagent of the present invention, the additive is a reducing agent.

IF$_5$-pyridine-HF and the additive contained in the fluorinating reagent of the present invention are those explained in the production method of the present invention.

The form of the fluorinating reagent of the present invention is not limited as long as the fluorinating reagent contains IF$_5$-pyridine-HF and the additive. For example, the fluorinating reagent may be a mixture of IF$_5$-pyridine-HF and the additive, or a kit in which IF$_5$-pyridine-HF and the additive are separated from each other.

The additive contained in the fluorinating reagent of the present invention is preferably Et$_3$N-nHF (wherein n is a real number of 1 to 9).

The amount of the additive contained in the fluorinating reagent of the present invention is preferably in the range of 0.01 to 10 mol, more preferably in the range of 0.1 to 5 mol, and even more preferably in the range of 0.1 to 2 mol per mol of the IF$_5$-pyridine-HF.

Advantageous Effects of Invention

The production method or fluorinating reagent of the present invention can provide, with a high yield, a fluorinated organic compound that has not been produced with a sufficient yield by a conventional method using a fluorinating agent containing IF$_5$-pyridine-HF alone.

Examples of the fluorinated organic compound that have not been produced with a sufficient yield by a conventional method include compounds with a larger fluorine amount. Specific examples of the compounds include trifluoromethyl 4-isopropyl phenyl ether,
1-bromo-4-(trifluoromethoxy)benzene,
ethyl 4-(trifluoromethoxy)benzoate,
1-(trifluoromethoxy)decane,
(3-(trifluoromethoxy)propyl)benzene,
ethyl 3-((4-chlorophenyl)thio)-2,2,3-trifluoropropanate,
4-pentyl-4'-(trifluoromethoxy)-1,1'-bi(cyclohexane),
1-fluoro-2-iodocyclododecane,
5-fluoro-6-iododecane, and
(Z)-2-fluoro-1-iodododecan-1-ene.

DESCRIPTION OF EMBODIMENTS

The present invention is detailed below with reference to the Examples; however, it is not limited to the Examples.

Example 1-1

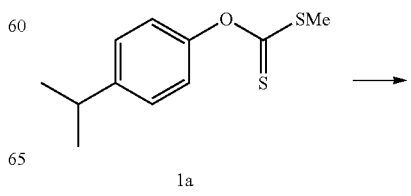

1a

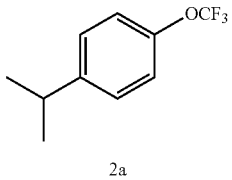

2a

In air, IF$_5$-pyridine-HF (370 mg, 1.15 mmol) and Et$_3$N-6HF (1.15 mmol) were added to methylene chloride (2 mL) in a Teflon (trade name) container, and compound 1a (O-(4-isopropyl phenyl)S-methyl dithiocarbonate) (0.5 mmol) was added thereto at room temperature, followed by stirring at 60° C. for six hours. The reaction mixture was added to water (20 mL), and extraction was performed using methylene chloride three times (20 mL×3). The organic layer was washed with a saturated sodium bicarbonate aqueous solution (20 mL) and a saturated sodium thiosulfate aqueous solution (20 mL), and then dried with magnesium sulfate. After condensation, product 2a (trifluoromethyl 4-isopropyl phenyl ether) was obtained by silica gel column chromatography (hexane ether) with a yield of 70%.

Example 1-2

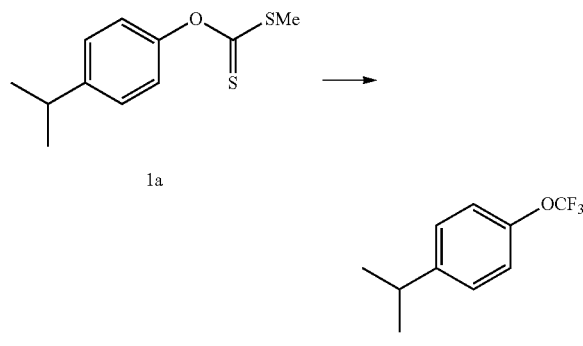

In air, IF$_5$-pyridine-HF (321 mg, 1.00 mmol) and Et$_3$N-6HF (553 mg, 2.50 mmol) were added to methylene chloride (1 mL) in a Teflon (trade name) container, and compound 1a (O-(4-isopropyl phenyl)S-methyl dithiocarbonate) (0.5 mmol) was added thereto at room temperature, followed by stirring at 60° C. for nine hours. The reaction mixture was added to water (30 mL), and extraction was performed using methylene chloride three times (20 mL×3). The organic layer was washed with a saturated sodium bicarbonate aqueous solution (20 mL) and a saturated sodium thiosulfate aqueous solution (20 mL), and then dried with magnesium sulfate. After condensation, product 2a (trifluoromethyl 4-isopropyl phenyl ether) was obtained by silica gel column chromatography (hexane ether) with a yield of 74%.

Comparative Example 1

In air, IF$_5$-pyridine-HF (321 mg, 1.00 mmol) was added to methylene chloride (1 mL) in a Teflon (trade name) container, and compound 1 (0.5 mmol) was added thereto at room temperature, followed by stirring at 60° C. for nine hours. The reaction mixture was added to water (30 mL), and extraction was performed using methylene chloride three times (20 mL×3). The organic layer was washed with a saturated sodium bicarbonate aqueous solution (20 mL) and a saturated sodium thiosulfate aqueous solution (20 mL), and then dried with magnesium sulfate. After condensation, product 2 was obtained by silica gel column chromatography (hexane ether) with a yield of 4%.

It is obvious from the comparison of Example 1-1 and Comparative Example 1 that the use of additive Et$_3$N-6HF remarkably increased the yield of product 2 in Example 1-1.

Comparative Example 2

In air, IF$_5$ (1.00 mmol), pyridine-HF (pyridine 1.00 mmol, HF 7.00 mmol), and Et$_3$N (1.00 mmol) were added to methylene chloride (1 mL) in a Teflon (trade name) container, and compound (0.5 mmol) was added thereto at room temperature, followed by stirring at 60° C. for nine hours. The reaction mixture was added to water (20 mL), and extraction was performed using methylene chloride three times (20 mL×3). The organic layer was washed with a saturated sodium bicarbonate aqueous solution (20 mL) and a saturated sodium thiosulfate aqueous solution (20 mL), and then dried with magnesium sulfate. After condensation, product 2 was obtained by silica gel column chromatography (hexane ether) with a yield of 41%.

It is obvious from the comparison of Example 1-1 and Comparative Example 2 that although IF$_5$, pyridine, HF, and triethylamine were used in Comparative Example 2 in the same molar ratio as in Example 1-1, and the same reaction temperature, reaction time, and purification method were employed, product 2 was not obtained with a sufficient yield. This indicates that product 2 was not obtained with a high yield merely by adding Et$_3$N as an additive to the reaction system.

TABLE 1

|  | Fluorinating reagent | ![OCF3 structure] 2 |
|---|---|---|
| Example 1-1 | (IF$_5$-Py-HF) + (Et$_3$N—6HF) | Yield 70% |
| Comparative Example 1 | (IF$_5$-Py-HF) | Yield 4% |
| Comparative Example 2 | IF$_5$ + Py + 7HF + Et$_3$N | Yield 41% |

Example 2

Products were synthesized in the same manner as in Example 1, except that the substrate (compound 1a), reaction temperature, time, and solvent used in Example 1-1 were changed to those shown in Table 2.

Regarding the "yield/%" in Table 2, the $^{19}$F-NMR yield is based on the substrate. The value in parenthesis is an isolation yield.

TABLE 2

| Substrate | Temperature/ °C. | Time/ h | Solvent | Product | Yield/ % |
|---|---|---|---|---|---|
| 1b | 60 | 24 | (CH$_2$Cl)$_2$ | 2b | 70 |
| 1c | 60 | 24 | (CH$_2$Cl)$_2$ | 2c | 65(55) |
| 1d | r.t. | 2 | CH$_2$Cl$_2$ | 2d | 93(91) |
| 1e | r.t. | 3 | CH$_2$Cl$_2$ | 2e | 100(67) |
| 1f | 0 | 24 | CH$_2$Cl$_2$ | 2f | (70) |

Example 3s

Polyfluorination Reaction of Alkyl Sulfide

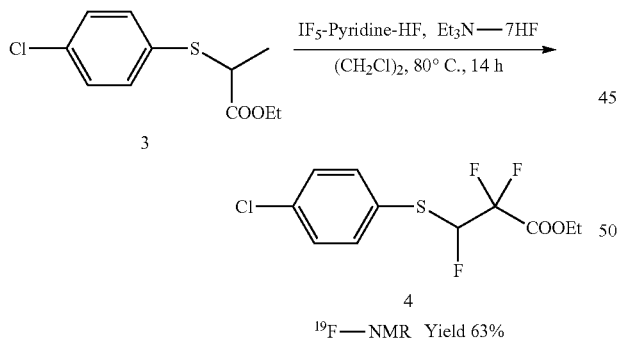

$^{19}$F—NMR Yield 63%

IF$_5$-pyridine-HF (321 mg, 1 mmol) and dichloroethane (2.0 mL) were added to a Teflon (trade name) reaction vessel with a lid. Three drops of Et$_3$N·7HF (54 mg, 0.22 mmol) were added thereto at room temperature. Subsequently, substrate 3 (122 mg, 0.5 mmol) was added thereto, followed by reaction at 80° C. for 14 hours. The reaction mixture was poured into water (30 mL) in a polycontainer, and neutralized with saturated NaHCO$_3$ water, followed by ether extraction. After dehydration with magnesium sulfate, the solvent was removed under reduced pressure. An internal standard (monofluorobenzene) was added to the residue, and the product was quantified by $^{19}$F-NMR. The results indicate that trifluoro body 4 was produced with a yield of 63%.

Example 4

Addition to Alkene (1)

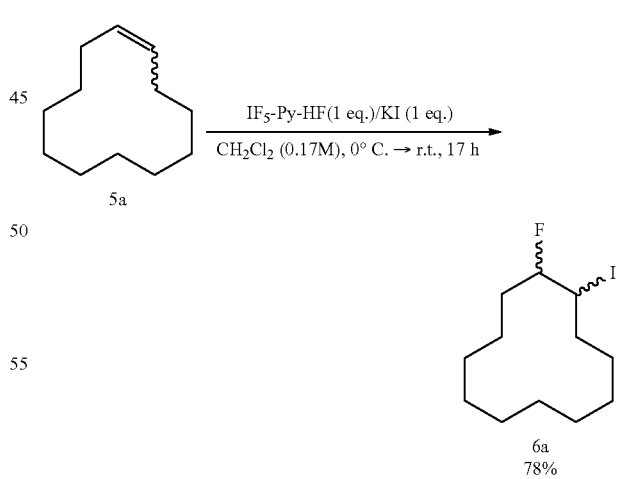

A substrate (alkene 5a, 0.5 mmol), methylene chloride (3 mL), and IF$_5$-pyridine-HF (161 mg, 0.5 mmol) were added to a Teflon (trade name) container, and KI (83 mg, 0.5 mmol) was added thereto while stirring the mixture at 0° C. The mixture was then stirred at 0° C. for 30 minutes, and at room temperature for 17 hours. After the reaction, product 6a was extracted with methylene chloride, and purified by silica gel column chromatography (ethyl acetate-hexane) to obtain product 6a with a yield of 78%.

Example 5

Addition to Alkene (2)

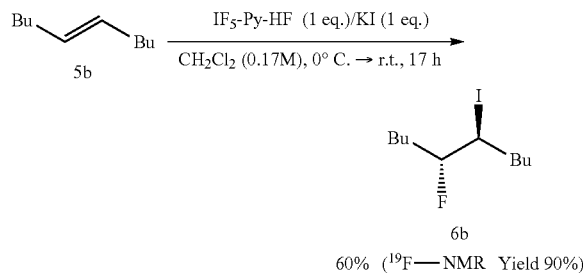

6b
60% ($^{19}$F—NMR Yield 90%)

A substrate (alkene 5b, 0.5 mmol), methylene chloride (3 mL), and IF$_5$-pyridine-HF (161 mg, 0.5 mmol) were added to a Teflon (trade name) container, and KI (83 mg, 0.5 mmol) was added thereto while stirring the mixture at 0° C. The mixture was then stirred at 0° C. for 30 minutes, and at room temperature for 17 hours. After the reaction, product 6b was extracted with methylene chloride, and purified by silica gel column chromatography (ethyl acetate-hexane) to obtain product 6b with a yield of 60%. The $^{19}$F-NMR yield was 90%.

Example 6

Addition to Alkyne

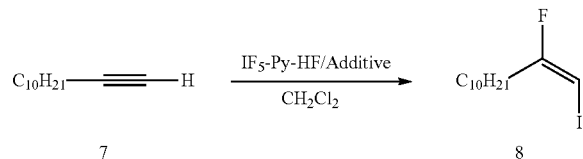

Alkyne 7 (0.5 mmol), IF$_5$-pyridine-HF (1.0 mmol, 320 mg), and dichloroethane (5 mL) were added to a Teflon (trade name) container, and the mixture was stirred at 0° C. for 20 minutes. An additive shown in Table 3 (hydroquinone (1.0 mmol, 110 mg) or catechol (1.0 mmol, 110 mg) was added thereto, and the mixture was further stirred at 0° C. for 30 minutes, and at room temperature for 12 hours. After extraction with dichloroethane, isolation and purification was performed by silica gel column chromatography (ethyl acetate-hexane). Table 3 shows the yield of product 8.

In Table 3, regarding the "yield/%," the $^{19}$F-NMR yield was based on the substrate. The value in parenthesis is the isolation yield.

TABLE 3

| Additive | 8 Yield/% |
|---|---|
| Hydroquinone | 82 (63) |
| Catechol | 75 |

Example 7

Products were synthesized in the same manner as in Example 6, except that the substrate (compound 7), amount of IF$_5$-pyridine-HF, additive, time, and reaction solvent used in Example 6 were changed to those shown in Table 4.

Regarding the "yield/%" in Table 4, the $^{19}$F-NMR yield is based on the substrate. The value in parenthesis is an isolation yield.

TABLE 4

| Substrate | IF$_5$-pyridine-HF | Additive | Time/h | Solvent | Product | Yield/% |
|---|---|---|---|---|---|---|
| Ph—≡—H 7b | 1.5 eq. | Hydroquinone 1.5 eq. | 9 | CH$_2$Cl$_2$ | 8b | 56 |
| Ph—≡—Ph 7c | 2.0 eq. | Hydroquinone 2.0 eq. | 15 | CH$_2$Cl$_2$ | 8c | 90(72) |
| Pr—≡—Pr 7d | 2.0 eq. | Hydroquinone 2.0 eq. | 15 | CH$_2$Cl$_2$ | 8d | 87 |
| AcO-(CH$_2$)$_9$-≡—H 7e | 2.0 eq. | Hydroquinone 2.0 eq. | 19 | CH$_2$Cl$_2$ | 8e | 73 |

TABLE 4-continued

| Substrate | IF$_5$-pyridine-HF | Additive | Time/h | Solvent | Product | Yield/% |
|---|---|---|---|---|---|---|
| 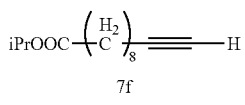<br>7f | 2.0 eq. | Hydroquinone 2.0 eq. | 20 | CH$_2$Cl$_2$ | 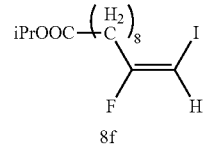<br>8f | 72 |
| 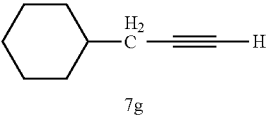<br>7g | 2.0 eq. | Hydroquinone 2.0 eq. | 20 | CH$_2$Cl$_2$ | 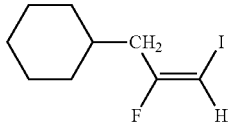<br>8g | 67 |

The invention claimed is:

1. A method for producing a fluorinated organic compound comprising step A of fluorinating an organic compound by bringing the organic compound into contact with (1) IF$_5$-pyridine-HF and (2) at least one additive selected from the group consisting of amine hydrogen fluorides, X$^a$F (wherein X$^a$ represents hydrogen, potassium, sodium, or lithium), oxidizers, and reducing agents, wherein the amount of the IF$_5$-pyridine-HF used in step A is in the range of 1 to 10 mol per mol of the organic compound, the reaction temperature of step A is in the range of −20 to 140° C., and the reaction time of step A is in the range of 0.5 to 48 hours.

2. The method according to claim 1, wherein the additive is Et$_3$N-nHF (wherein n is a real number of 1 to 9).

3. A fluorinating reagent comprising (1) IF$_5$-pyridine-HF and (2) at least one additive selected from the group consisting of amine hydrogen fluorides, X$^a$F (wherein X$^a$ represents hydrogen, potassium, sodium, or lithium), oxidizers, and reducing agents.

4. The fluorinating reagent according to claim 3, wherein the additive is Et$_3$N-nHF (wherein n is a real number of 1 to 9).

* * * * *